(12) United States Patent
Han et al.

(10) Patent No.: US 11,202,685 B2
(45) Date of Patent: Dec. 21, 2021

(54) SYSTEM FOR IDENTIFYING POSITION OF MARKER FOR ORTHOPEDIC SURGERY AND METHOD FOR IDENTIFYING SAME

(71) Applicant: CUREXO, INC., Seoul (KR)

(72) Inventors: Yonghee Han, Ulsan (KR); Donggi Woo, Ulsan (KR); Junwoo Park, Ulsan (KR)

(73) Assignee: CUREXO, INC., Seoul (KR)

( * ) Notice: Subject to any disclaimer, the term of this patent is extended or adjusted under 35 U.S.C. 154(b) by 398 days.

(21) Appl. No.: 15/776,480

(22) PCT Filed: Nov. 14, 2016

(86) PCT No.: PCT/KR2016/013065
§ 371 (c)(1),
(2) Date: May 16, 2018

(87) PCT Pub. No.: WO2017/090924
PCT Pub. Date: Jun. 1, 2017

(65) Prior Publication Data
US 2018/0333214 A1    Nov. 22, 2018

(30) Foreign Application Priority Data

Nov. 27, 2015 (KR) .................. 10-2015-0167396

(51) Int. Cl.
*A61B 34/35* (2016.01)
*A61B 34/20* (2016.01)
(Continued)

(52) U.S. Cl.
CPC .............. *A61B 34/35* (2016.02); *A61B 34/20* (2016.02); *A61B 34/30* (2016.02); *A61B 90/00* (2016.02);
(Continued)

(58) Field of Classification Search
CPC ......... A61B 34/35; A61B 34/20; A61B 34/30; A61B 90/00; A61B 90/06;
(Continued)

(56) References Cited

U.S. PATENT DOCUMENTS

2006/0058604 A1   3/2006  Avinash et al.
2006/0258938 A1  11/2006  Hoffman et al.
(Continued)

FOREIGN PATENT DOCUMENTS

JP    2000-271888      10/2000
JP    2008-538184 A    10/2008
(Continued)

OTHER PUBLICATIONS

International Search Report for International Application No. PCT/KR2016/013065, dated Feb. 14, 2017.

*Primary Examiner* — Marcela I. Shirsat
(74) *Attorney, Agent, or Firm* — Novick, Kim & Lee, PLLC; Jae Youn Kim; Jihun Kim (57) ABSTRACT

The present invention relates to a system and method for identifying position of marker for orthopedic surgery, wherein the system comprises a main sensor and an auxiliary sensor having different sensing schemes, so that during orthopedic surgery, it is possible to flexibly handle a situation where a single sensor fails or a sensing signal cannot be received, thereby accurately identifying the position and posture of a marker.

13 Claims, 7 Drawing Sheets

(51) Int. Cl.
*A61B 34/30* (2016.01)
*A61B 90/00* (2016.01)
*A61B 17/00* (2006.01)

(52) U.S. Cl.
CPC ..... *A61B 90/06* (2016.02); *A61B 2017/00115* (2013.01); *A61B 2017/00119* (2013.01); *A61B 2034/2048* (2016.02); *A61B 2034/2055* (2016.02); *A61B 2034/2057* (2016.02); *A61B 2090/067* (2016.02); *A61B 2090/0818* (2016.02); *A61B 2090/3983* (2016.02); *A61B 2560/0266* (2013.01)

(58) Field of Classification Search
CPC .... A61B 2034/2048; A61B 2034/2055; A61B 2034/2057; A61B 2090/067; A61B 2090/0818; A61B 2090/3983; A61B 90/30; A61B 2017/00119; A61B 2017/00017; A61B 2017/00115; A61B 2034/2068; A61B 34/25; A61B 34/10; A61B 2560/0266; B60L 2250/10
USPC ........................................................ 606/102
See application file for complete search history.

(56) References Cited

U.S. PATENT DOCUMENTS

| | | | |
|---|---|---|---|
| 2007/0265527 | A1* | 11/2007 | Wohlgemuth ......... A61B 6/547 600/424 |
| 2012/0205419 | A1* | 8/2012 | Weir .................... A61B 17/068 227/2 |
| 2014/0088410 | A1 | 3/2014 | Wu |
| 2016/0361125 | A1* | 12/2016 | Balicki ................... B25J 19/06 |

FOREIGN PATENT DOCUMENTS

| | | |
|---|---|---|
| JP | 5743495 | 7/2015 |
| KR | 10-1154100 | 6/2012 |
| KR | 10-2013-0015441 | 2/2013 |
| KR | 10-1336005 | 12/2013 |
| KR | 10-2014-0056772 | 5/2014 |
| KR | 10-2014-0065541 | 5/2014 |
| KR | 10-2015-0000279 | 1/2015 |
| KR | 10-1527176 | 6/2015 |
| WO | 00/39576 A1 | 7/2000 |
| WO | 2006/091494 A1 | 8/2006 |

* cited by examiner

SYSTEM FOR IDENTIFYING POSITION OF MARKER FOR ORTHOPEDIC SURGERY AND METHOD FOR IDENTIFYING SAME

FIELD OF THE INVENTION

The present invention relates to technique for identifying the position of orthopedic surgical marker, and more specifically, system and method which uses a main sensor and an auxiliary sensor having different sensing mode to flexibly handle abnormal status of single sensor failure or signal receipt error and accurately identify the position and the posture of the marker for the orthopedic surgery.

BACKGROUND OF THE INVENTION

As medical technique develops nowadays, navigation surgery with robots and computer system has been introduced more actively, and applied to the field of artificial joint surgery.

As for knee joint, when pain and behavior disorder resulted from any infections or injury, orthopedic surgery cures the knee joint by replacing whole or part of the knee joint, and 10-30% of the patients suffer the abrasion of knee inner joint and have the partial replacement surgery of the knee joint.

Automatic driving CAD/CAM robot, which is a kind of ROBODOC, can be one example of a robot for the orthopedic joint surgery. Those orthopedic surgical robots cut a bone along pre-planned route and therefore fixing the bone is important while cutting.

On the process of knee replacement surgery with the orthopedic surgical robot so far, as published on Korean Patent registration gazettes No. 10-1154100 (2012 May 31), some optical marker is installed, the position and the posture of the optical marker are tracked by optical sensor of a navigator with monitoring the operation, and then the surgical robot is put on the accurate surgical site.

However, in surgical process, a robot arm of the surgical robot, movements of medical team, and other obstacles might block sight of the optical sensor of the navigator so as not to identify the position of the patient or the surgical robot. In this case, as the surgery should be stopped and the operation of the optical sensor should be inspected, the surgery is problematically delayed.

Recently, as Korean patent publication No. 10-2014-0056772 (2012 Oct. 13) discloses, it is applied that operator handles the operational part of an interventional procedure robot for inserting needle ('needle inserting robot').

DETAILED DESCRIPTION OF THE INVENTION

Technical Problem

The present invention is to solve the aforementioned problems of the prior technique, and the purpose of the system and method for identifying position of the marker for orthopedic surgery according to the present invention is to provide a system with main sensor and auxiliary sensor having different sensing mode for tracking the position and the posture of the marker in real time even when main sensor or auxiliary sensor operates abnormally.

Technical Solution

The system for identifying position of marker for orthopedic surgery according to the present invention comprises: a sensor part installed near surgical site and on an orthopedic surgical robot, and including first sensor and second sensor; first position detecting part for detecting the position of the first sensor; second position detecting part for detecting the position of the second sensor; and a control part for receiving position signals detected by the first position detecting part and the second position detecting part to set the first sensor and the second sensor as main sensor or auxiliary sensor based on the operational status of the first sensor and the second sensor.

The method for identifying position of marker for orthopedic surgery according to the present invention comprises the steps of (a) detecting the position of first sensor of a sensor part with first position detecting part and the position of second sensor of the sensor part with second position detecting part, wherein the sensor part is installed near surgical site and on one part of a surgical robot; (b) receiving position signals detected by the first and second position detecting parts to locate the position of auxiliary sensor in the coordinate system of the sensor which is set as main sensor with a sensor-position matching part of a control part; and (c) tracking the position and the posture of the sensor part with a position tracking part.

Advantageous Effect of the Invention

As explained above, the present invention of system and method for identifying position of marker for orthopedic surgery can track the position and the posture of the marker even when main sensor and auxiliary sensor operate abnormally, and therefor minimize surgical suspensions and react rapidly and actively to sensor detecting failure by controlling the speed of the orthopedic surgical robot according to the abnormal operation of the sensor.

DETAILED DESCRIPTION OF EXEMPLARY EMBODIMENTS

Hereinafter, the detailed contents to carry out the system and method for identifying position of marker for orthopedic surgery according to the present invention will be described.

Figure 1:
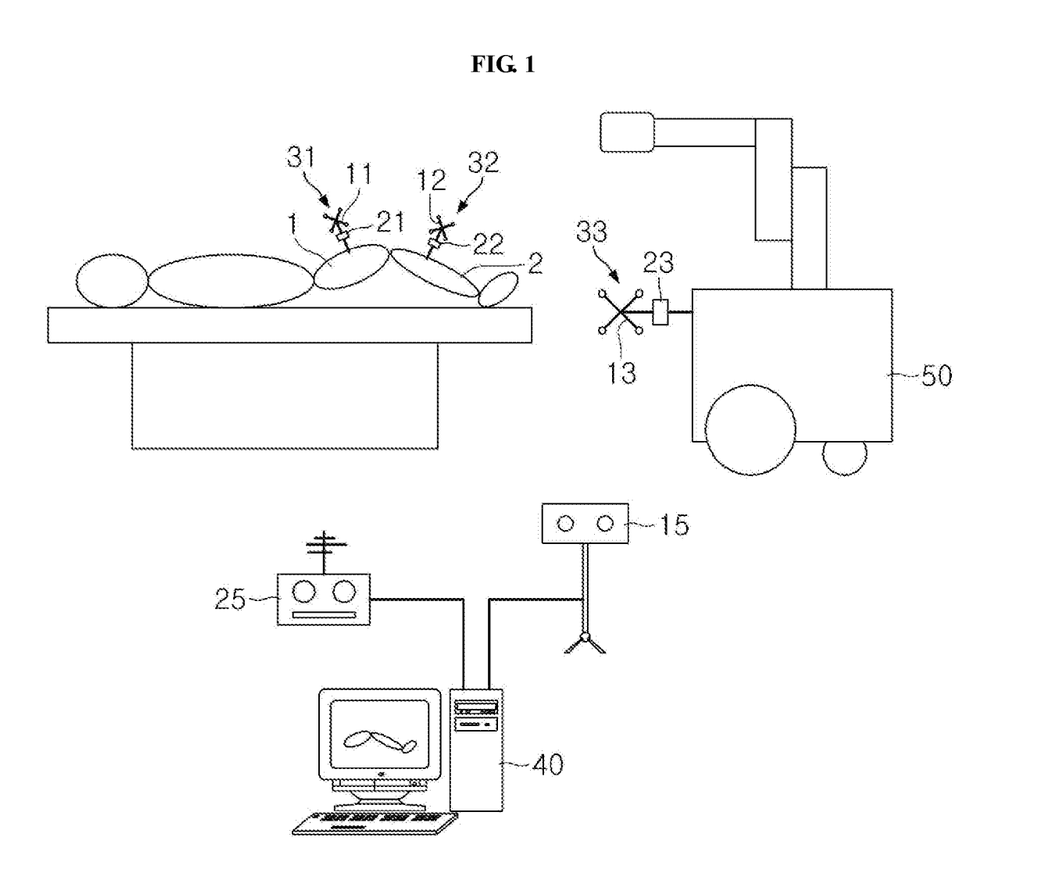
FIG. 1 is a drawing of a whole composition of the system for identifying position of marker for orthopedic surgery according to the present invention.

FIG. 1 is a drawing of a whole composition of the system for identifying position of marker for orthopedic surgery according to the present invention, comprising a sensor part 3, first position detecting part 15, second position detecting part 25, a control part 40, and an orthopedic surgical robot 50.

The sensor part 3 comprises the first sensor member 31 installed at a femur 1, the second sensor member 32 installed at a tibia 2, and the third sensor member 33 installed at the orthopedic surgical robot 50, and each of the sensor members 31, 32, 33 comprises each of first sensors 11, 12, 13 and each of second sensors 21, 22, 23 which has a tilt sensor and an acceleration sensor.

In exemplary embodiment of the present invention, the first sensor 11, 12, 13 might be an optical marker with three or four bars extending in different direction from the center point, and ball markers with high-reflectivity are installed at the end of the bars.

The first position detecting part 15 is an optical tracking sensor which detects the position and the posture of the first sensor 11, 12, 13 on a three-dimensional coordinate space, and sends the detected signals to the control part 40. In this embodiment, the first position detecting part 15 is embodied in a stereo infrared camera.

The second sensor 21, 22, 23 includes the tilt sensor and the acceleration sensor inside, detects the positions of the first sensors 11, 12, 13 with the tilt sensor, and reduces error of the tilting signal to acquire position information of the first sensor 11, 12, 13 complementarily.

The second position detecting part 25 is a sensor signal receiver to detect the positions of the second sensors 21, 22, 23 with the signals sent from the second sensor 21, 22, 23. The position signals detected by the second position detecting part 25 will be sent to the control part 40.

The control part 40 receives the position signals detected by the first position detecting part 15 and the second position detecting part 25, locates the position of the first sensor 11, 12, 13 and the second sensor 21, 22, 23 on same coordinate system, and sets up main sensor and auxiliary sensor based on the operational status of the first sensor 11, 12, 13 and the second sensor 21, 22, 23.

Figure 2:
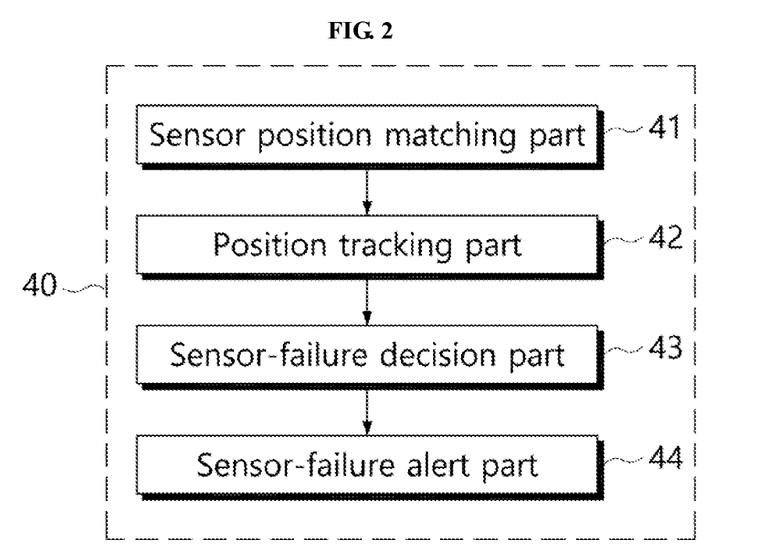
FIG. 2 is a drawing of detailed composition of the control part of the system for identifying position of marker for orthopedic surgery according to the present invention.

The control part 40 according to the present invention comprises a sensor-position matching part 41 for receiving the position signals, which is detected by the first position detecting part 15 and the second position detecting part 25, to locate the position of auxiliary sensor in the coordinate system of main sensor, a position tracking part 42 to track the positions and the postures of the first sensor member 31, the second sensor member 32 and the third sensor member 33, a sensor-failure decision part 43 to set a normal operative sensor as main sensor when the first position detecting part 15 or the second position detecting part 25 operates abnormally, and a sensor-failure alert part 44 to display a sensor-failure notification when the sensor failure occurs. Abnormal operation of the first position detecting part 15 might be caused by the damage or destruction of at least one of the first sensor 11, 12, 13 or the first position detecting part 15. Also, Abnormal operation of the second position detecting part 25 might be caused by the damage or destruction on at least one of the second sensor 21, 22, 23 or the first position detecting part 25.

According to the present invention, the sensor-failure decision part 43 can generate robot stopping signal or robot decelerating signal and send it to the orthopedic surgical robot 50 when at least one of the first position detecting part 15 or the second position detecting part 25 operates abnormally.

The operation of the system for identifying position of marker for orthopedic surgery according to the present invention is explained as below.

Figure 3:
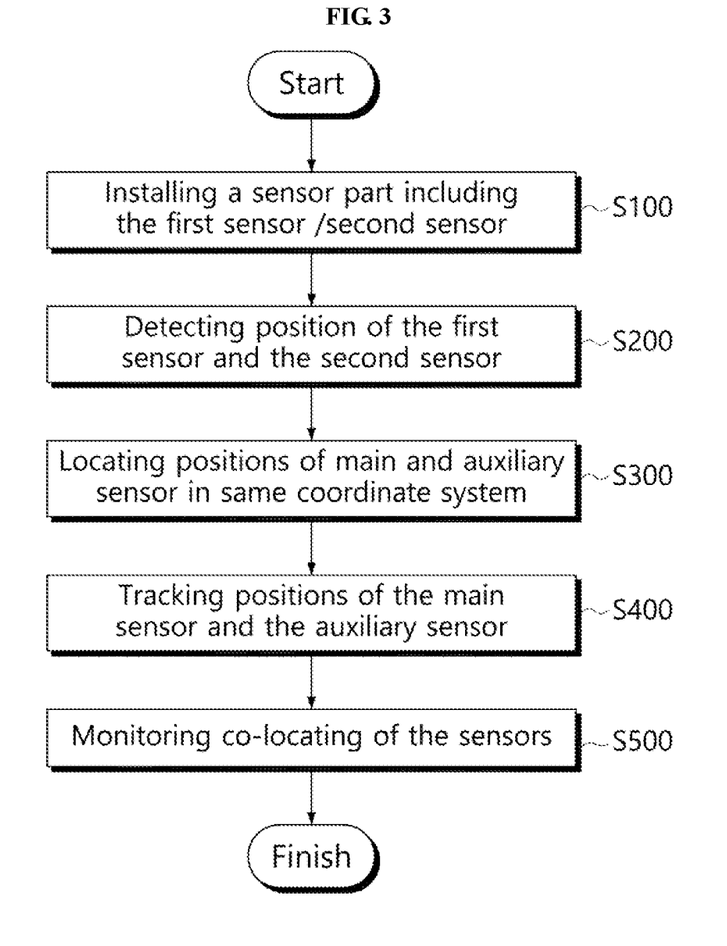
FIG. 3 is a flowchart of the method for identifying position of marker for orthopedic surgery according to the present invention.

FIG. 3 is a flowchart of the method for identifying position of marker for orthopedic surgery according to the present invention.

The method according to the embodiment of the present invention comprises a step S100 of installing the sensor part 3. That is, the first sensor member 31 is installed at a femur 1, the second sensor member 32 is installed at a tibia 2, and the third sensor member 33 is installed at the orthopedic surgical robot 50

After that, in step S200, the first detecting part 15 detects the positions of the first sensors 11, 12, 13 of the sensor members 31, 32, 33 installed near the surgical site, and the second sensor detecting part 25 detects the positions of the second sensors 21, 22, 23 of the sensor members 31, 32, 33.

Next, the sensor position matching part 41 of the control part 40 receives the position signals detected by the first position detecting part 15 and the second position detecting part 25 and locates the position of auxiliary sensor in the coordinate system of sensor which is set as main sensor in step S300.

Figure 4:
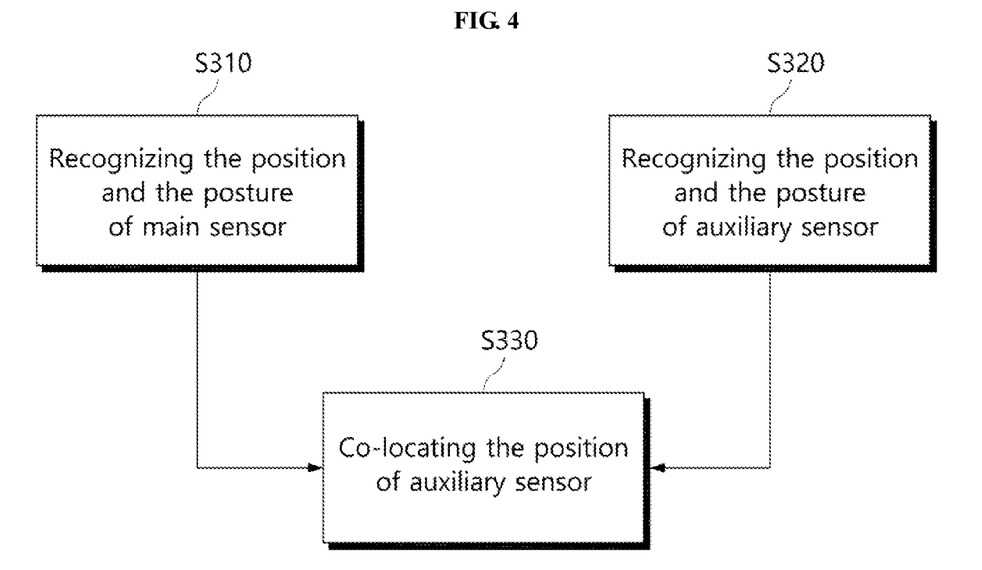
FIG. 4 is a flowchart of a detailed flow of step S300 of the method for identifying position of marker for orthopedic surgery according to the present invention.
Figure 5:
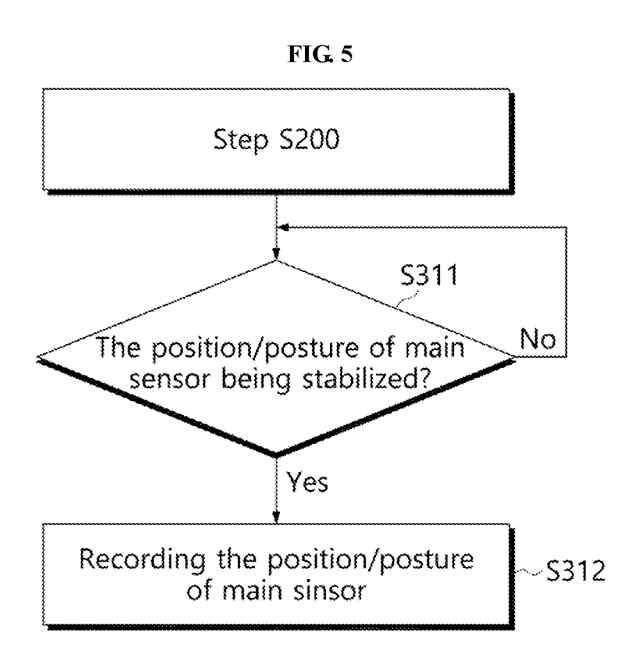
FIG. 5 is a flowchart of a detailed flow of step S310 of the method for identifying position of marker for orthopedic surgery according to the present invention.

As shown in FIG. 4, the step S300 might comprise a step S310 of detecting the position and the posture of the first sensors 11, 12, 13 of the sensor members 31, 32, 33 based on the position signals detected by the first position detecting part 15, which is set as main sensor. Also, as shown in FIG. 5, the step S310 according to the present invention might comprise a step S311 of checking whether or not the variation of position signals detected by the first position detecting part 15 is lower than a preset threshold value, and a step S312 of recording the position and the posture of the first sensors 11, 12, 13 when the variation of position signals detected by the first position detecting part 15 is lower than the threshold value in the step S311. The step S311 of checking whether or not the variation of the position signals detected by the first position detecting part 15 is lower than the threshold value can also be performed by determining whether the position and the posture of the first sensor 11, 12, 13, which is detected by the first position detecting part 15, is stabilized or not.

In step S320 at the same time with the step S310, the second position detecting part 25, which is set as auxiliary sensor, acquires the position signals of the second sensors 21, 22, 23.

In step S320, the second sensors 21, 22, 23, which include the tilt sensor and the acceleration sensor, detect the position of the first sensor with the tilt sensor and reduce errors of the tilt signal with output signal of the acceleration sensor, which helps to acquire position information of the first sensors 11, 12, 13 complementarily.

And then, in step S330, the positions of the second sensors 21, 22, 23, which is detected by the second position detecting part 25 set as the auxiliary sensor, are located in the coordinate system of the first sensor 11, 12, 13.

After that, in step S400, tracking the position and the posture of the first sensor member 31, the second sensor member 32, and the third sensor member 33 with the position tracking part 42 is operated.

Figure 6:
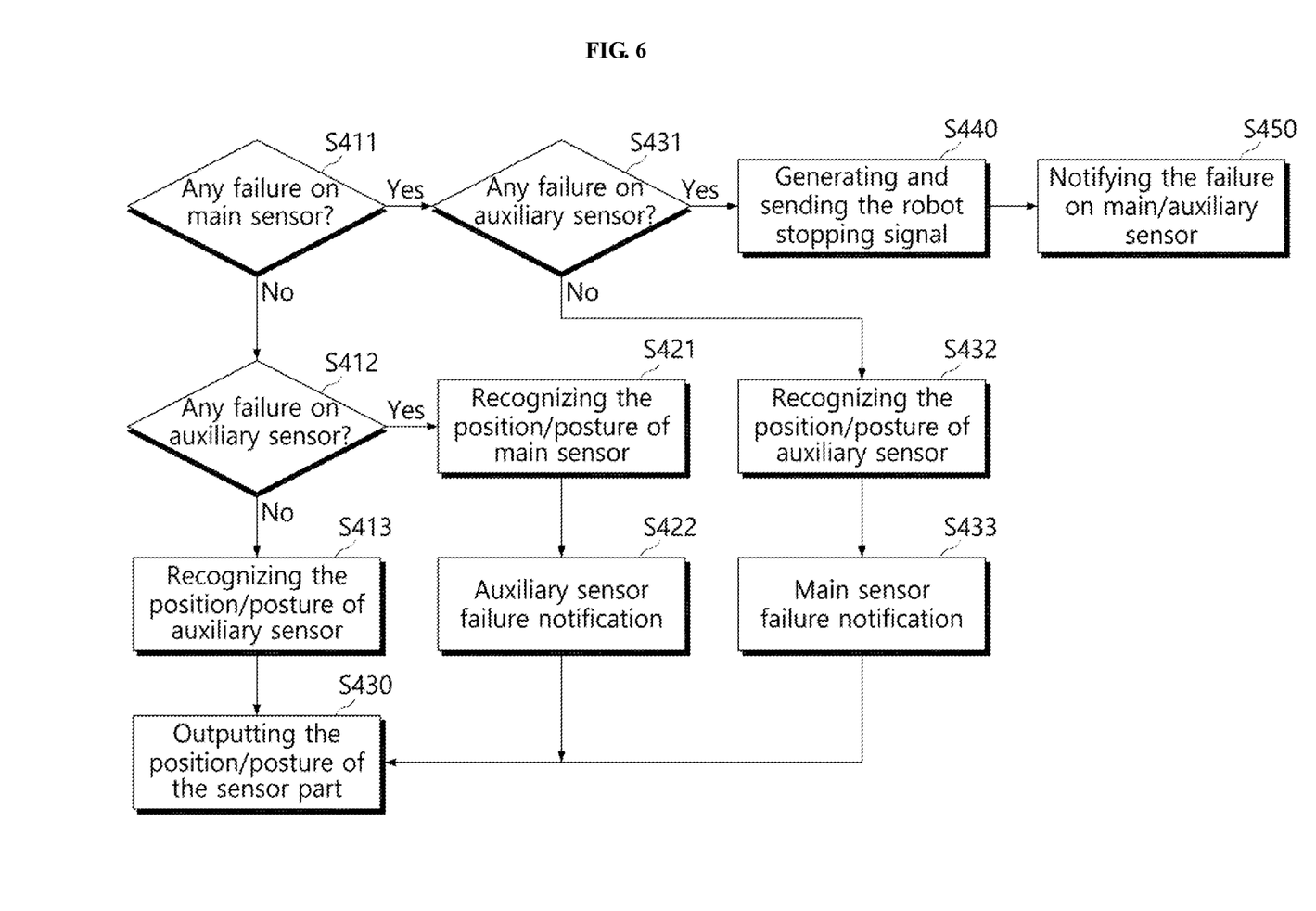
FIG. 6 is a flowchart of a detailed flow of step S400 of the method for identifying position of marker for orthopedic surgery according to the present invention.

The step S400 according to the present invention, as shown in FIG. 6, operates step S411 of determining whether or not the first position detecting part 15 of the main sensor operates normally with sensor-failure decision part 43, and step S412 of determining whether the second position detecting unit 25 of the auxiliary sensor operates normally or not when the normal operation of the first position detecting part 15 is determined in the step S411. If the normal operation of the second position detecting part 25 is determined in the step S412, then, in steps 413 and 430, the position and the posture of the first sensor 11, 12, 13 are recognized based on the position signals detected by the first position detecting part 15 and the second position detecting part 25 and output. Herein, the step S412 of determining whether or not the operation of the second position detecting part 25 is normal can be implemented by determining whether or not the operations of the second sensors 21, 22, 23 are normal.

Also, if the abnormal operation of the second position detecting part 25 is determined in the step S412, then in step S421 the position and the posture of the first sensor 11, 12, 13 are recognized based on detection of the first position detecting part 15 of the main sensor, in step S422 the failure notification of the second position detecting part 25 of the auxiliary sensor is displayed by the sensor-failure alert part 44, and in step S430 the detected position and the posture of the first sensor 11, 12, 13 are output.

If the abnormal operation of the first position detecting part 15 is determined in the step S411, in step S431 whether or not the operation of the second position detecting part 25 is normal is determined. As a result, if the normal operation of the second position detecting part 25 is determined in the step S431, then in step S432 the position and the posture of the first sensor 11, 12, 13 detected by the second position detecting part 25 of the auxiliary sensor are recognized, and in step S433 the failure notification of the first position detecting part 15 of the main sensor is displayed by the sensor-failure alert part 44, and in the step S430 the detected position and the posture of the first sensors 11, 12, 13 are output.

In addition, if the abnormal operation of the first position detecting part 15 determined in the step S411, then in the step S431 whether or not the operation of the second position detecting part 25 is normal is determined. As a result, if the abnormal operation of the second position detecting part 25 is determined in the step S431, then in step S440 robot stopping signal is generated and sent to the orthopedic surgical robot 50, and in step S450 failure notification of the first position detecting part 15 of the main sensor and the second position detecting part 25 of the auxiliary sensor are displayed by the sensor-failure alert part 44.

Figure 7:
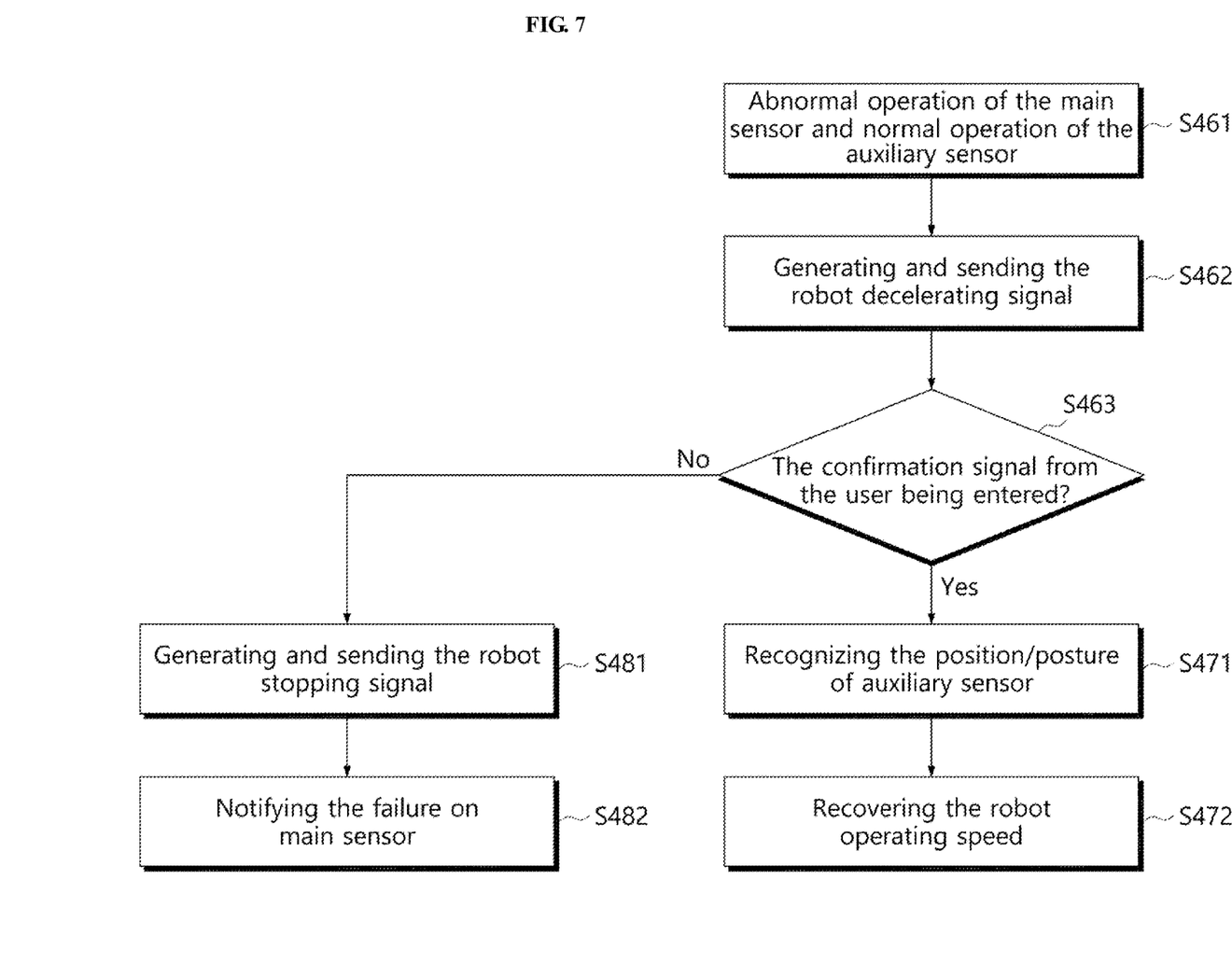
FIG. 7 is a flowchart of another detailed flow of step S400 of the method for identifying position of marker for orthopedic surgery according to the present invention.

FIG. 7 shows another exemplary embodiment of the step S400, wherein if the sensor-failure decision part 43 determines the abnormal operation of the first position detecting part 15 and the normal operation of the second position detecting part 25 in step S461, then robot stopping signal is generated and sent to the orthopedic surgical robot in step S462, it is checked if a user enters a confirmation within preset time in step S463, and then if so the position and the posture of the first sensor 11, 12, 13 are output based on the position signals detected by the second position detecting part 25 in step S471, and the recover signal of the robot operation speed is generated and sent to the orthopedic surgical robot in step S472.

In addition, if the user confirmation signal is not entered within the preset time in the step S463, then robot stopping signal is generated and sent to the orthopedic surgical robot 50 in step S481, and the failure notification of the first position detecting part 15 is displayed by the sensor-failure alert part 44 in step S482.

As explained above, according to the system and method for identifying position of marker for orthopedic surgery of the present invention, the position and posture of the marker can be tracked in real time even when the main sensor or the auxiliary sensor operates abnormally.

Furthermore, the surgical suspensions can be minimized, and the sensor detecting failure can be rapidly and actively reacted to by controlling the speed of the orthopedic surgical robot according to the abnormal operation of the sensors.

Even though the exemplary embodiments of the present invention have been explained above, the present invention is not limited to the embodiments above, and the system and method for identifying position of marker for orthopedic surgery can be realized in various way within the technical idea of the present invention.

What is claimed is:

1. A system for identifying a position of an optical marker for orthopedic surgery, the system comprising:
    a sensor part configured to be disposed on an object, and including the optical marker and a sensor;
    a first position detector for detecting the position of the optical marker;
    a second position detector for detecting a position of the sensor;
    a controller for setting one of the first position detector or the second position detector as a main sensor and the other as an auxiliary sensor, and for tracking the position of the optical marker based on position signals detected by the main sensor and the auxiliary sensor; and
    an orthopedic surgical robot,
    wherein the controller is configured to:
    generate a robot decelerating signal and send the robot decelerating signal to the orthopedic surgical robot when a failure of the main or auxiliary sensor occurs;
    check if a user enters a confirmation within a preset time after sending the robot decelerating signal to the orthopedic surgical robot;
    recognize the position of the marker based on a position signal of the main or auxiliary sensor one of which is operating normally when the confirmation is entered within the preset time; and
    generate a recover signal of a robot operation speed and send the recover signal to the orthopedic surgical robot.

2. The system for identifying the position of the optical marker for orthopedic surgery according to claim 1, wherein the controller is further configured to:
    determine a failure of the first position detector and the second position detector,
    display a sensor-failure notification message when the failure occurs, and
    set the position detector set as the auxiliary sensor as the main sensor when a failure of the position detector set as the main sensor occurs and the position detector set as the auxiliary sensor operates normally.

3. The system for identifying the position of the optical marker for orthopedic surgery according to claim 2, the controller is further configured to recognize the position of the optical marker based only on the position signals of the position detector set as the main sensor.

4. The system for identifying the position of the optical marker for orthopedic surgery according to claim 1, wherein the controller is further configured to generate a robot stopping signal and to send the robot stopping signal to the orthopedic surgical robot when a failure of the main sensor and a failure of the auxiliary sensor occur.

5. The system for identifying the position of the optical marker for orthopedic surgery according to claim 1, wherein the controller is further configured to generate a robot stopping signal and to send the robot stopping signal to the orthopedic surgical robot if the confirmation is not entered.

6. A method for identifying a position of a marker for orthopedic surgery by a computer system, the method comprising:
- setting one of a first position detector or a second position detector as a main sensor and the other as an auxiliary sensor;
- detecting position signals for the marker by the main sensor and the auxiliary sensor;
- tracking the position of the marker based on the position signals detected by the main sensor and the auxiliary sensor;
- generating a robot decelerating signal and sending the robot decelerating signal to an orthopedic surgical robot when a failure of the main or auxiliary sensor occurs;
- displaying a sensor-failure notification message;
- checking, by the computer system, if a user enters a confirmation within a preset time after sending the robot decelerating signal to the orthopedic surgical robot;
- recognizing the position of the marker based on a position signal of the main or auxiliary sensor one of which is operating normally when the confirmation is entered within the preset time; and
- generating a recover signal of a robot operation speed and sending the recover signal to the orthopedic surgical robot.

7. The method for identifying the position of the marker for orthopedic surgery according to claim 6, the method further comprising:
- generating a robot stopping signal and sending the robot stopping signal to the orthopedic surgical robot if the confirmation is not entered.

8. The method for identifying the position of the marker for orthopedic surgery according to claim 6, the method further comprising:
- determining whether the main sensor and the auxiliary sensor operate normally or not; and
- recognizing the position of the marker based on the position signals of the auxiliary sensor when an abnormal operation of the main sensor and a normal operation of the auxiliary sensor are determined.

9. The method for identifying the position of the marker for orthopedic surgery according to claim 6, the method further comprising:
- recognizing the position of the marker detected by the main sensor when a normal operation of the main sensor and an abnormal operation of the auxiliary sensor are determined.

10. The method for identifying the position of the marker for orthopedic surgery according to claim 6, the method further comprising:
- generating a robot stopping signal and sending the robot stopping signal to the orthopedic surgical robot when a failure of the main sensor and a failure of the auxiliary sensor occur.

11. A method for identifying a position of a marker for orthopedic surgery by a computer system, the method comprising:
- setting one of a first position detector or a second position detector as a main sensor and the other as an auxiliary sensor;
- detecting position signals for the maker by the main sensor and the auxiliary sensor;
- tracking the position of the marker based on the position signals detected by the main sensor and the auxiliary sensor;
- determining whether the main sensor operates normally or not;
- determining whether the auxiliary sensor operates normally or not when an abnormal operation of the main sensor is determined;
- generating a robot decelerating signal and sending the robot decelerating signal to the orthopedic surgical robot when a normal operation of the auxiliary sensor is determined;
- checking, by the computer system, if a user enters a user's confirmation signal within a preset time;
- recognizing the position of the marker based on the position signal of the auxiliary sensor when the user's confirmation signal is entered within the preset time; and
- generating a recover signal of a robot operation speed and sending the recover signal to the orthopedic surgical robot.

12. The method for identifying the position of the marker for orthopedic surgery according to claim 11, the method further comprising:
- generating a robot stopping signal and sending the robot stopping signal to the orthopedic surgical robot when the user's confirmation signal is not entered within the preset time; and
- displaying a failure notification of the main sensor.

13. The method for identifying the position of the marker for orthopedic surgery according to claim 11, the method further comprising:
- generating a robot stopping signal and sending the robot stopping signal to the orthopedic surgical robot when a failure of the main sensor and a failure of the auxiliary sensor occur.

* * * * *